(12) United States Patent
Mizutani et al.

(10) Patent No.: US 7,179,247 B2
(45) Date of Patent: Feb. 20, 2007

(54) ABSORBABLE ARTICLE WITH PROTRUDING BODY FLUID INFLOW HOLE HAVING AN ELASTIC SIDE WALL

(75) Inventors: Satoshi Mizutani, Kagawa (JP); Koichi Yamaki, Kagawa (JP); Yuki Noda, Kagawa (JP)

(73) Assignee: Uni-Charm Corporation, Kawanoe (JP)

( * ) Notice: Subject to any disclaimer, the term of this patent is extended or adjusted under 35 U.S.C. 154(b) by 0 days.

(21) Appl. No.: 10/888,430

(22) Filed: Jul. 8, 2004

(65) Prior Publication Data

US 2005/0027277 A1    Feb. 3, 2005

Related U.S. Application Data

(63) Continuation of application No. PCT/JP02/12018, filed on Nov. 18, 2002.

(51) Int. Cl.
*A61F 13/471* (2006.01)
*A61F 13/536* (2006.01)

(52) U.S. Cl. ............... 604/385.101; 604/380; 604/383; 600/574

(58) Field of Classification Search ......... 604/385.101, 604/39, 331, 385.01, 383, 385.17, 395, 329–330, 604/378–380, 346, 358, 349; 383/36; 220/571, 220/404; 600/574–575
See application file for complete search history.

(56) References Cited

U.S. PATENT DOCUMENTS

| 4,270,539 A | * | 6/1981 | Frosch et al. ............. 604/347 |
| 4,421,511 A | * | 12/1983 | Steer et al. ............... 604/329 |
| 4,484,917 A | * | 11/1984 | Blackmon ................. 604/327 |
| 4,634,440 A | * | 1/1987 | Widlund et al. ........... 604/383 |
| 4,778,459 A | * | 10/1988 | Fuisz ........................ 604/378 |
| 4,988,345 A | * | 1/1991 | Reising ..................... 604/368 |
| 5,062,840 A | * | 11/1991 | Holt et al. ............. 604/385.19 |
| 5,161,544 A | * | 11/1992 | Morris ...................... 128/849 |
| 5,267,988 A | * | 12/1993 | Farkas ...................... 604/329 |
| 5,336,208 A | * | 8/1994 | Rosenbluth et al. ........ 604/329 |
| 5,462,541 A | * | 10/1995 | Bruemmer et al. ......... 604/391 |
| 5,810,798 A | * | 9/1998 | Finch et al. ............... 604/378 |
| 6,551,292 B1 | * | 4/2003 | D'Acchioli et al. ........ 604/329 |
| 2002/0010449 A1 | * | 1/2002 | Mizutani ................... 604/380 |
| 2003/0120178 A1 | * | 6/2003 | Heki ......................... 600/574 |

FOREIGN PATENT DOCUMENTS

| JP | 51-48395 A1 | 10/1949 |
| JP | 59-161821 A1 | 10/1984 |
| JP | 3-43833 A1 | 4/1991 |
| JP | 7-13319 A1 | 3/1995 |

(Continued)

*Primary Examiner*—Tatyana Zalukaeva
*Assistant Examiner*—Laura C. Hill
(74) *Attorney, Agent, or Firm*—Darby & Darby

(57) ABSTRACT

The present invention provides an absorbent article (14) used by being fitted to the female pubic region, which comprises: an absorbent sheet body made of a water permeable sheet (11), a water impermeable sheet (12), and an absorbent body (13) being formed into one body; and a body fluid inflow hole (14b) in a cylindrical shape with the garment side being the bottom, having an opening in a size capable of being fitted to cover a pair of labia majoras from outside.

7 Claims, 11 Drawing Sheets

FOREIGN PATENT DOCUMENTS

| | | | |
|---|---|---|---|
| JP | 09-299392 | A1 | 11/1997 |
| JP | 11-089867 | A1 | 4/1999 |
| JP | 11-290365 | A1 | 10/1999 |
| JP | 2000-135235 | A1 | 5/2000 |
| JP | 2000-201959 | A1 | 7/2000 |
| JP | 2002-282292 | A1 | 10/2002 |
| JP | 2003-038561 | A1 | 2/2003 |
| JP | 2003-038562 | A1 | 2/2003 |
| JP | 2003-038563 | A1 | 2/2003 |
| WO | WO-99/26578 | A1 | 6/1999 |
| WO | WO 00/00114 | A1 * | 1/2000 |

* cited by examiner

FIG. 5
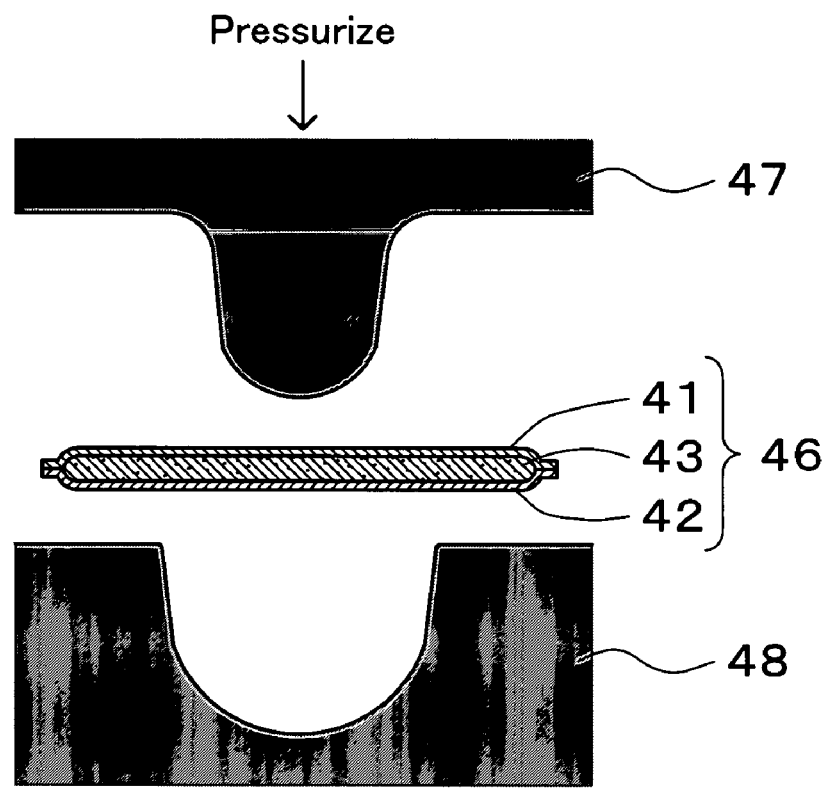
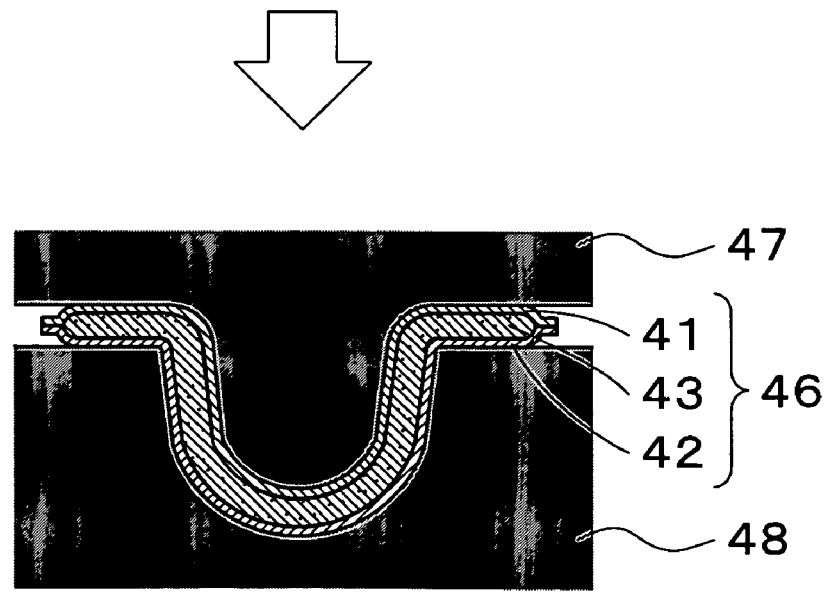

ABSORBABLE ARTICLE WITH PROTRUDING BODY FLUID INFLOW HOLE HAVING AN ELASTIC SIDE WALL

CROSS-REFERENCE TO RELATED APPLICATIONS

This application is a Continuation of International Application No. PCT/JP2002/012018 filed Nov. 18, 2002, which application published in Japanese on Jun. 3, 2004 as WO 2004/045479 A1 under PCT Article 21 (2).

FIELD OF THE INVENTION

The present invention relates to an absorbent article used in contact with the female pubic region.

BACKGROUND ART

Conventionally, a sanitary napkin that is used in contact with the female pubic region has been used for a female sanitary product in general. However, the napkin is used through being adhered to a garment and does not closely come into contact with the ostium vaginae area. Therefore, it is likely to generate a leak (side leak) of menstrual blood from the gap between the body and napkin, there is a fear that the garment may be stained.

As a sanitary product effective to prevent such a side leak, for example, a sanitary napkin 24 as shown in FIG. 2 is proposed (Japanese Patent Laid-Open No. 1991-43833).

The sanitary napkin 24 is provided with a ring-shaped protrusion 24a on the body side face of the napkin, thereby to prevent the side leak of menstrual blood by surely catching the menstrual blood through a hole part 24b formed by the ring-shaped protrusion 24a. In accordance with the sanitary napkin 24, it is relatively not likely to generate the side shift when a wearer does not make much movement such as exercises and walking. Thus, the menstrual blood is guided to the hole part 24b inside the ring-shaped protrusion 24a, thereby decreasing a risk of causing the side leak.

However, the sanitary napkin 24 moves together with the underclothing to which the sanitary napkin 24 is attached, when the wearer makes the movements such as exercises and walking. Thus, the position shift is easily generated between the pubic region and the hole part 24b, and it cannot completely prevent the side leak when the wearer moves, so there is a fear that the garment may be stained.

Further, as a sanitary product effective to prevent the side leak, for example, a sanitary napkin 34 as shown in FIG. 3 is also proposed (Japanese Utility Model Laid-Open No. 1995-13319).

The sanitary napkin 34 comprises a water impermeable flap 36 with elasticity provided on a body side of a napkin main body and an adhesion portion 37 provided on the body side face of the flap 36. By adhering the adhesion portion 37 to the body, a three-dimensional wall with water impermeability is formed between the body and the napkin main body, thereby effectively preventing the side leak. Therefore, it has an advantage that the garment is not stained even when the wearer makes the movements such as exercises and walking.

However, as for the sanitary napkin 34, due to its structure, the napkin main body comes into contact with a wide range of the skin from the vestibule to the haunches. Therefore, the menstrual blood is to be attached to the wide range of the skin, thereby causing a rough skin.

Further, the sanitary napkin 34 is formed relatively bulky so as to prevent the deformation. Thus, it has a disadvantage in regards to giving an uncomfortable wearing feeling to the body over a wide range. Especially, when the wearer engages in exercises, walking or the like, the sanitary napkin 34 receiving motion stress and the flap 36 fitted to the body are to be deformed. Thus, the body (skin) to which the flap 36 is fixed via an adhesive 37 is being pulled together, so that the wearing feeling is further deteriorated.

The present invention has been designed to overcome the foregoing subjects. An object of the present invention is to provide an absorbent article which can prevent the side leak of the body fluid such as the menstrual blood so as not to stain the garment and, at the same time, restrict the contact between the discharged body fluid and the skin as much as possible, thereby to obtain a comfortable wearing feeling.

DISCLOSURE OF THE INVENTION

In order to overcome the foregoing subjects, in the absorbent article of the present invention, a body fluid inflow hole is provided. By providing the body fluid inflow hole, the body fluid such as the menstrual blood discharged form the ostium vaginae directly flows into the body fluid inflow hole without traveling through the surface of the absorbent article and is absorbed within the menstrual blood inflow hole. As a result, the side leak of the body fluid can be prevented, thereby preventing the garment from being stained. Thus, it can prevent the contact between the discharged body fluid and the skin as much as possible, so that a comfortable wearing feeling can be achieved.

To be more specific, the present invention provides an absorbent article as is described below.

(1) An absorbent article comprising an absorbent sheet body, the sheet body being integrally composed of an water permeable sheet facing a body side of a wearer and a water permeable or water impermeable sheet facing a garment side such that an absorbent body capable of absorbing body fluid is contained in between the sheets, wherein the article is applied to a pubic region, the article comprising: a body fluid inflow hole formed into a cylindrical shape with a bottom on the garment side and an opening on the body side with a size capable of fitting a pair of labia majoras from outside such that the pair of labia majoras pass through the opening.

The absorbent article is used in such a manner that a pair of labia majoras is fitted to the opening of the body fluid inflow hole. By fitting it in this manner, the body fluid (especially the menstrual blood) discharged from the ostium vaginae is directly and quickly guided to the body fluid inflow hole without traveling through the surface of the absorbent article. Therefore, it can prevent the menstrual blood from traveling through the surface of the absorbent article and causing the side leak. Thereby, the garment is not to be stained.

Moreover, since the discharged menstrual blood flows into the body fluid inflow hole which is not in contact with the skin of the wearer, the contact between the discharged menstrual blood and the skin of the wearer is restricted. Thus, it enables to avoid such a case that the menstrual blood sticks to the skin in a wide range from the vestibule to the haunches causing a rough skin. Further, by providing a swollen part serving for the, body fluid inflow hole in the absorbent article, it enables to increase the bulkiness and the surface area of the absorbent body as the whole portion of the absorbent article while reducing the bulkiness of the part out of the absorbent article to be in contact with the skin of the wearer. Thus, it becomes possible to achieve a comfortable wearing feeling without deteriorating the absorbing capacity of the absorbent article.

The absorbent article is provided with the body fluid inflow hole formed into a cylindrical shape with a bottom on the garment side. For example, in an absorbent article 44 shown in FIG. 4, a body fluid inflow hole 44b of a cylindrical shape with an oval-shaped bottom on the garment side of the absorbent article is formed in a substantially flat area 44a. The "cylindrical shape" in the present specification refers to any shape having a hollow internal space, and is not limited to the one with the same bottom and opening shapes. For example, it may be a conical shape in which the bottom shape gradually expands or a bowl shape in which the bottom shape gradually decreases.

It is preferable that, in order for the labia to be surely covered inside, the shape of the opening of the body fluid inflow hole has a shape substantially longer in the longitudinal direction. It is more preferable that the shape be a long oval so as to be fitted with the shape of the labia. The opening is formed to have a size capable of being fitted to cover a pair of labia majoras from outside so that the absorbent article can be worn through fitting a pair of labia majoras thereto. Specifically, it is preferable that the length be within the range of 60 to 180 mm, more preferable to be within the range of 80 to 150 mm, and furthermore preferable to be within the range of 90 to 130 mm. As for the width, it is preferable to be within the range of 20 to 60 mm, and more preferable to be within the range of 30 to 50 mm.

As shown in FIG. 5, the absorbent article provided with such body fluid inflow hole can be formed relatively easily by a method of pressurizing an adsorbent sheet body 46, which is formed by laminating a water permeable sheet 41, an absorbent body 43, and a water impermeable sheet 42, through pinching it between a convex mold 47 and a concave mold 48 which have been heated.

(2) The absorbent article according to (1), comprising an adhesion portion surrounding a periphery of the opening of the body fluid inflow hole on the body side face of the absorbent article.

For example, as shown in FIG. 6, by forming an adhesion portion 50 in the body side face of the adsorbent article 44 (more specifically, in the substantially flat area 44a), the absorbent article 44 can be more securely brought into contact with the pubic region. In such a condition, generation of a gap between the absorbent article 44 and the body or a position shift of the absorbent article caused by a sudden change in the body position of the wearer can be prevented. Therefore, it becomes possible to more surely guide the body fluid (especially the menstrual blood) to the body fluid inflow hole 44b so that the wearer is not to be limited in the action but can enjoy any activities without anxiety. Normally, the adhesion portion 50 is formed along the periphery of the opening of the body fluid inflow hole 44b.

(3) The absorbent article according to (2), wherein the adhesion portion is divided into left and right parts with respect to a substantial center line of the absorbent article along a longitudinal direction.

The adhesion portion may be formed to surround the whole girth of the opening of the body fluid inflow hole or formed to surround a part of the opening of the body fluid inflow hole. For example, in the absorbent article 44 shown in FIG. 6, the adhesion portion 50 is provided to be separated in left and right parts with respect to a substantial center line 49 of the absorbent article 44 in the longitudinal direction. With this condition, the absorbent article 44, when receiving the motion stress of the wearer, is hard to be bound to the skin of the wearer and changes its shape relatively freely. Therefore, it can prevent the skin of the wearer from being pulled by the adhesive which forms the adhesion portion 50 so as not to deteriorate the wearing feeling. More specifically, it is preferable that end points 50a and 50b of the adhesion portion be separated in left and right parts with a space of 1 to 10 mm between the substantial center line 49 being the boundary.

(4) The absorbent article according to (2) or (3), wherein an elastic sheet body made of an elastically restoring material is interposed between the body side face of the absorbent article and the adhesion portion.

When the adhesion portion is formed in the body side face of the absorbent article, without taking any measure, it exhibits a low shape-following characteristic against deformation caused by pressurizing or torsion while the absorbent article is being worn. Therefore, the adhesion portion is crinkled and the adhesives forming the adhesion portion stick to each other. This is not preferable in respect that it deteriorates the wearing feeling of the absorbent article. In the absorbent article, for example, as shown in FIG. 7, an elastic sheet body 52 made of an elastic restoring material is interposed between the body side face of the absorbent article 44 (more specifically the substantially flat area 44a) and the adhesion portion 50. The elastic sheet body 52 gives flexibility to the adhesion portion 50 thereby improving the shape-following characteristic. Also, it enables to, even when the adhesion portion 50 is deformed, prevent the adhesion portion 50 from being kept in the deformed state so as to immediately recover to the initial state. As a result, it can avoid the state where the adhesives forming the adhesion portion stick to each other, thereby achieving a comfortable wearing feeling.

In the present specification, the "elastically restoring material" means a material with an elastic flexibility and a shape-recovery characteristic which immediately recover to the initial shape based on the elasticity after being deformed by stress.

(5) The absorbent article according to (2) or (3), wherein a corrugation processing is performed at least on a place where the adhesion portion is formed among on the body side face of the absorbent article.

In order to avoid a state where the adhesion portion is crinkled and the adhesives forming the adhesion portion stick to each other so that the wearing feeling of the absorbent article is deteriorated, in addition to interposing the elastic sheet body, for example, as shown in FIG. 8, corrugation processing 54 may be performed on at least a part where the adhesion portion 50 is formed. By performing the corrugation processing 54, pleats, in which concaves and convexes are continuously provided, are formed in the absorbent article in the lateral direction. Therefore, the shape-following characteristic against the deformation or torsion by pressure is improved while the absorbent article is being worn and the left and right parts of the absorbent article can change the shape of its phase separately. Further, the adhesion portion 50 is not to be pulled by the skin and stays in the initial adhered position as it is. Therefore, it enables to achieve a comfortable wearing feeling by avoiding the above-described state as in the case where the elastic sheet body is interposed. It is preferable to perform the corrugation processing in about 1 to 10 mm width from the opening of the body fluid inflow hole by a mechanical treatment.

(6) The absorbent article according to any one from (2) to (5), comprising an attachment tab of a band shape extending out from a side edge of the adhesion portion.

When the adhesion portion is formed in the body side face of the absorbent article, fingers may stick to the adhesion portion when wearing the absorbent article. In such a case, the absorbent article may be adhered in a state where the opening of the body fluid inflow hole is deformed or the position of the opening of the body fluid inflow hole is shifted from the right position. In order to avoid it, for example, as shown in FIG. 9, it is preferable to provide a band-shaped attachment tab 56 which is extended from the side edges of the adhesion portion 50 of the absorbent article 44. By wearing the absorbent article 44 through grabbing the attachment tab 56 with fingers from both sides, it becomes unlikely that the fingers touch the adhesion portion 50. Thereby, it enables to prevent the deformation or position shift generated in the opening of the body fluid inflow hole 44b. The attachment tab 56 is formed into a shape which is easily grabbed with fingers. It is preferable to have the size within the range of 10 to 30 mm in the longitudinal direction and 10 to 25 mm in the lateral direction.

(7) The absorbent article according to any one from (1) to (6), wherein a side wall of the body fluid inflow hole is composed of an elastically restoring material.

In the absorbent article, for example, as shown in FIG. 10, the side wall of the body fluid inflow hole 44b comprises an absorbent sheet body 46b (the water permeable sheet 41b, the absorbent body 43b, and the water impermeable sheet 42b) made of an elastically restoring material. Thus, even when the body fluid inflow hole 44b is deformed by pressurizing or torsion generated while the absorbent article is worn, it is not to be kept in the deformed state but immediately recovered to the initial shape. Therefore, the opening of the body fluid inflow hole 44b can be always kept in an open state so that it is always ready for receiving the inflow of the menstrual blood.

(8) The absorbent article according to any one from (1) to (7), wherein the absorbent body is contained in the water permeable sheet; and wherein the garment side face on the bottom of the body fluid inflow hole is lined with the water impermeable sheet.

A general example of the absorbent article of the present invention, as shown in FIG. 11, comprises the water permeable sheet 41 on the body side of the absorbent article, the water impermeable sheet 42 on the garment side, and the absorbent sheet body 46 in which the absorbent body 43 is included so as to be pinched between both sheets. However, as shown in FIG. 12, it may comprise the absorbent body 43 included in the water permeable sheet 41, and the absorbent sheet body 46 in which the garment side in the bottom face of the body fluid inflow hole 44b is lined with the water impermeable sheet 42. The reason is that most of the menstrual blood flown into the body fluid inflow hole 44b is absorbed in the bottom of the body fluid inflow hole 44b. Thus, it is sufficient to simply coat the bottom with the water impermeable sheet 42 so that the body fluid such as the menstrual blood is not to be permeated.

(9) The absorbent article according to any one from (1) to (8), wherein the whole adsorbent sheet is formed into a cylindrical shape with a bottom and a hollow part serves as the body fluid inflow hole.

In the present invention, as a general example as shown in FIG. 4, the absorbent article 44 is formed in such a manner that the body fluid inflow hole 44b is formed in a part of the substantially flat area 44a. However, for example, as shown in FIG. 13, the whole body of the absorbent sheet comprising the absorbent article 44 is formed into a cylindrical shape with a bottom so that the hollow serves for the body fluid inflow hole 44b. With such a condition, relatively a large-sized opening of the body fluid inflow hole 44b can be provided. Therefore, such an absorbent article has an advantage that it becomes capable of sufficiently coping with the cases where the wearer suffers from, for example, hypermenorrhea in which a person experiences a larger amount of the menstrual blood outflow at a higher rate compared to other people in general.

As an example of the detailed configuration of the absorbent article described in (9), as shown in FIG. 14, it may comprises the absorbent body 43 included between the water permeable sheet 41 and the water impermeable sheet 42, and the absorbent sheet body 46 with a configuration in which the side wall of the body fluid inflow hole 44b and the garment side face are coated with the water impermeable sheet 42.

(10) The absorbent article according to any one from (1) to (9), wherein the absorbent article is for incontinence.

The above-described absorbent article can be used as measures for incontinence support. In other words, since the ostium vaginae for discharging the menstrual blood and the urethra meatus for discharging urine are both between the labia so that, when the absorbent article according to the present invention is worn by fitting a pair of labia majoras to the opening of the body fluid inflow hole, urine is immediately guided to the body fluid inflow hole so that the contact between the discharged urine and the skin of the wearer can be prevented.

Thus, according to the present invention, an absorbent pad effective for incontinence, especially for a slight incontinence can be obtained, as it can guide urine to the body fluid inflow hole.

(11) The absorbent article according to any one from (1) to (9), wherein the absorbent article is for absorbing vaginal discharge.

According to such auxiliary pad for the absorbent article of the present invention, the auxiliary pad for the absorbent article can be used for absorbing the vaginal discharge. In short, as the auxiliary pad for the absorbent article according to the present invention is pinched between interlabia for use, it can absorb the discharge (vaginal discharge) other than menstrual blood from the ostium vaginae, so it can be used for this application (vaginal discharge absorption).

BRIEF DESCRIPTION OF THE DRAWINGS

FIG. 5 is a drawing showing the manufacturing process of the absorbent article;

PREFERRED EMBODIMENTS OF THE INVENTION

Next, embodiments of the absorbent article of the present invention shall be described referring to drawings.

Figure 1:
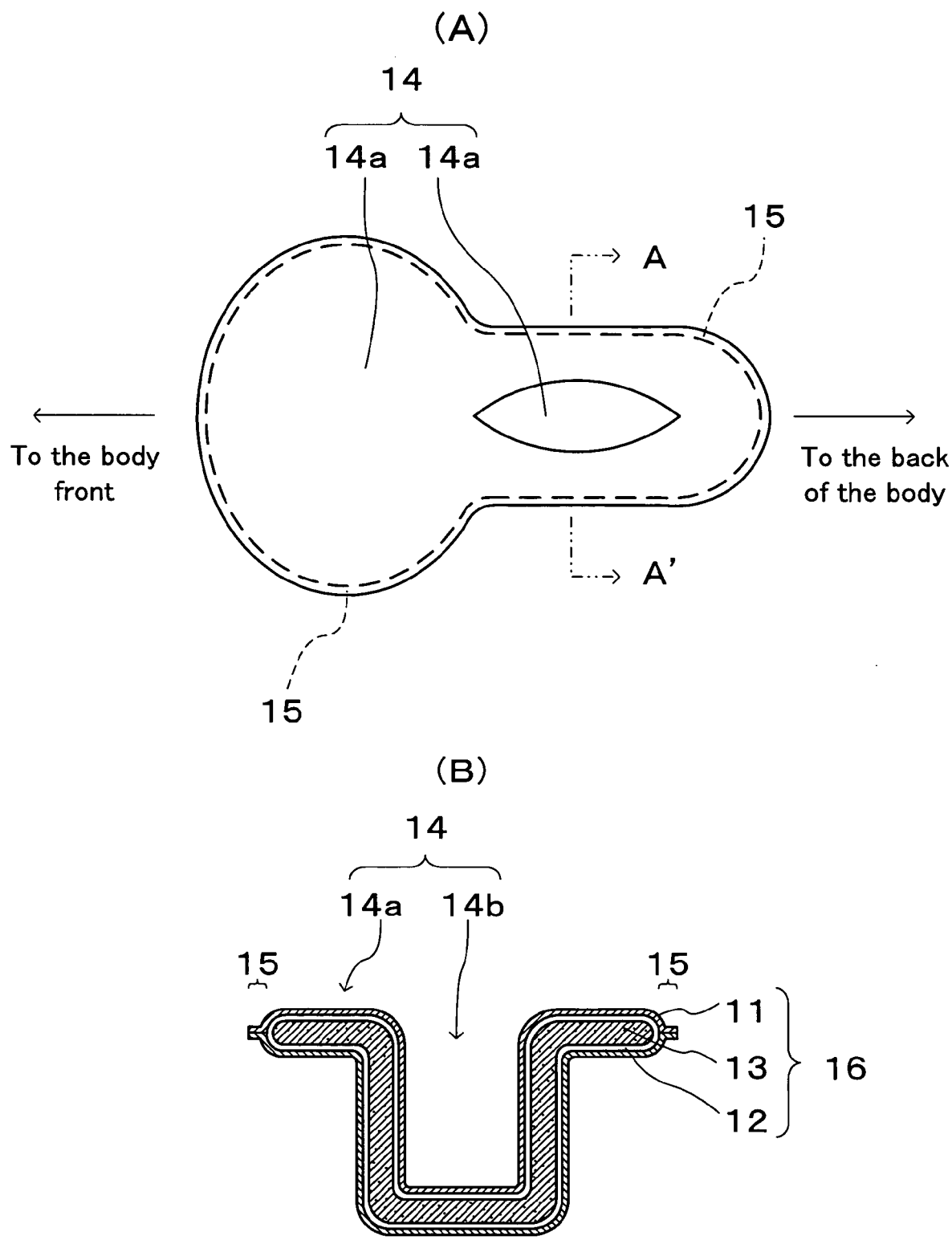
FIG. 1 is an illustration showing a structure of an absorbent article according to the present invention, (a) is a top view of the article, and (b) is a cross sectional view along the line A–A' in (a)
Figure 2:
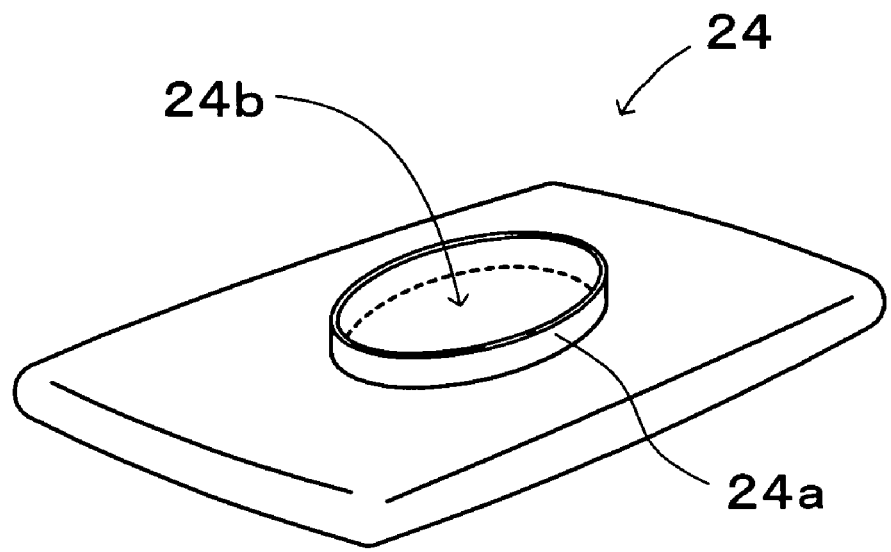
FIG. 2 is a perspective view showing a structure of a conventional sanitary napkin.
Figure 3:
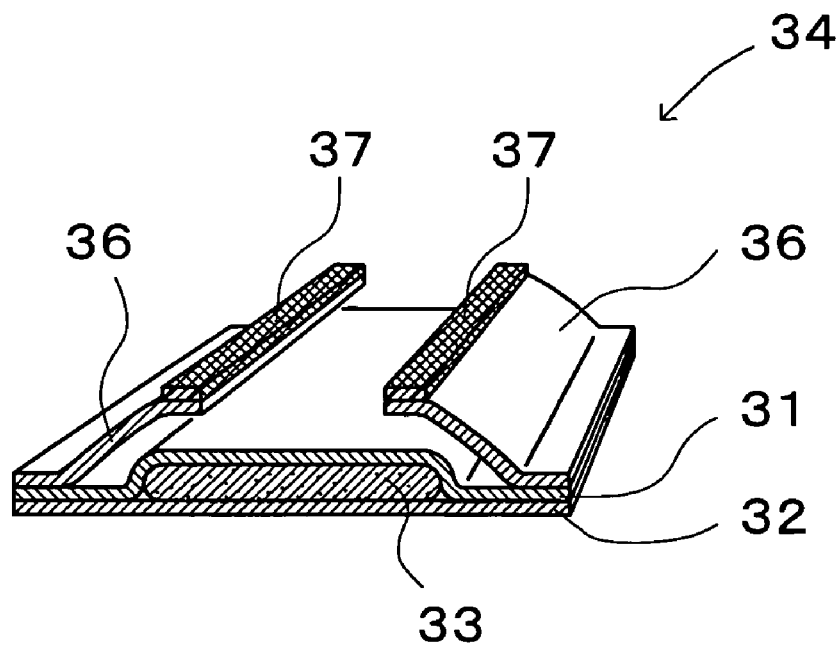
FIG. 3 is a perspective view showing the structure of the conventional sanitary napkin.
Figure 4:
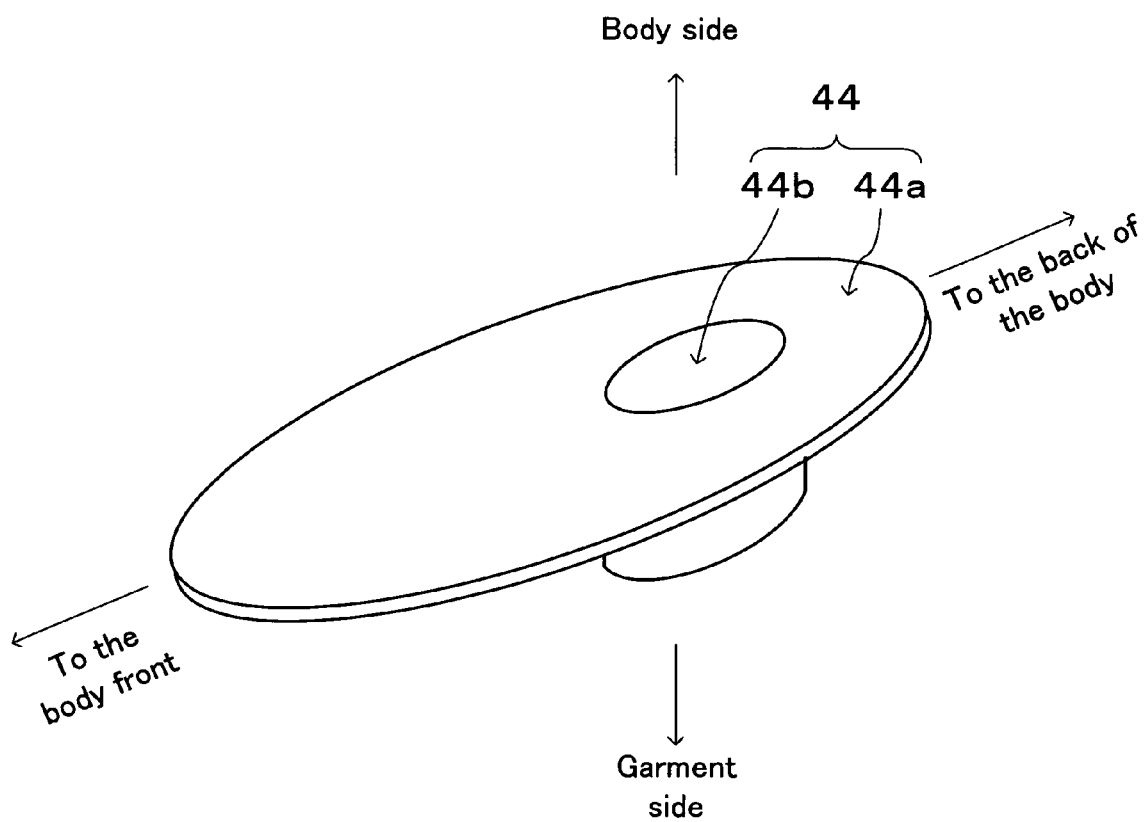
FIG. 4 is a perspective view showing a structure of the absorbent article according to the present invention.
Figure 6:
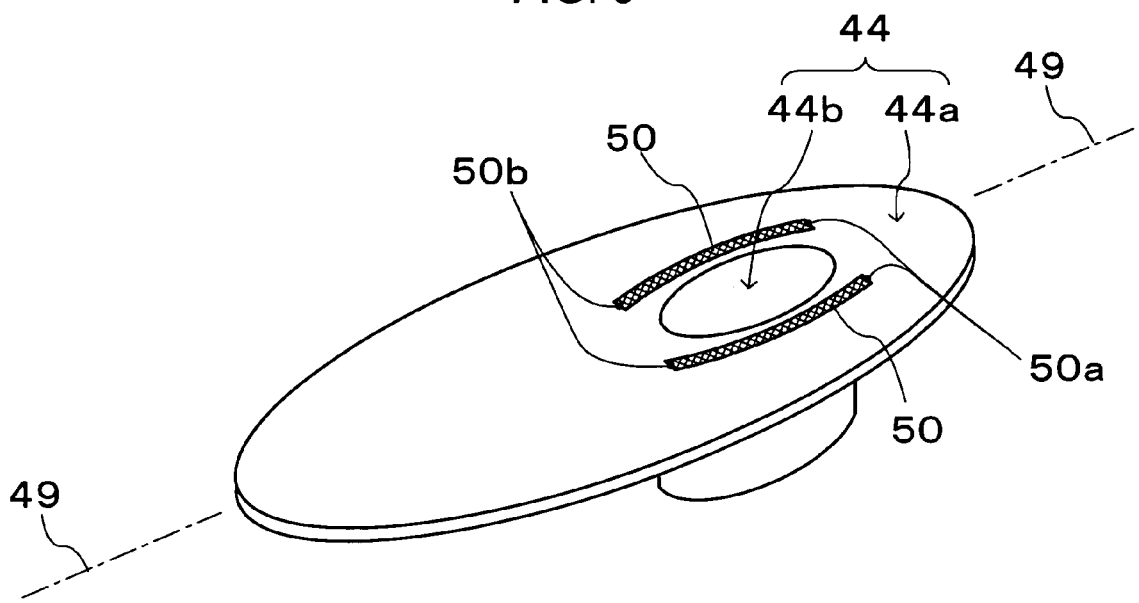
FIG. 6 is a perspective view showing a structure of the absorbent article according to the present invention.
Figure 7:
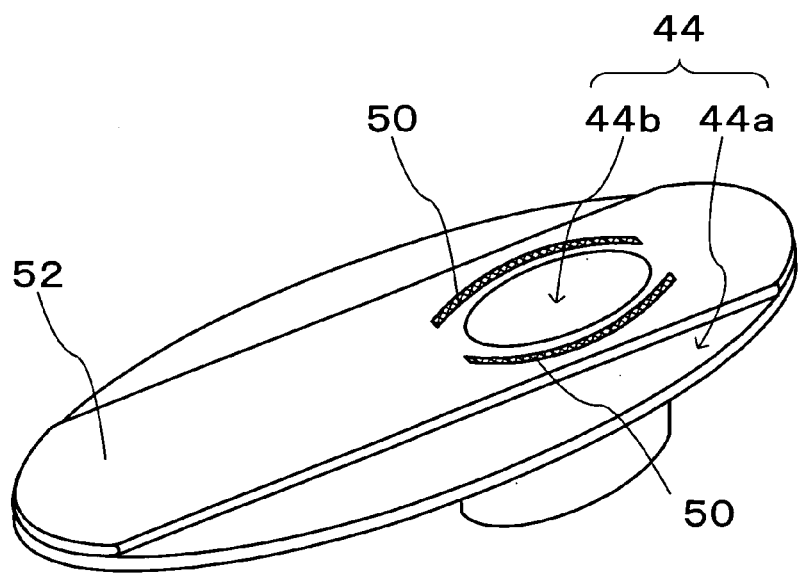
FIG. 7 is a perspective view showing the structure of the absorbent article according to the present invention.
Figure 8:
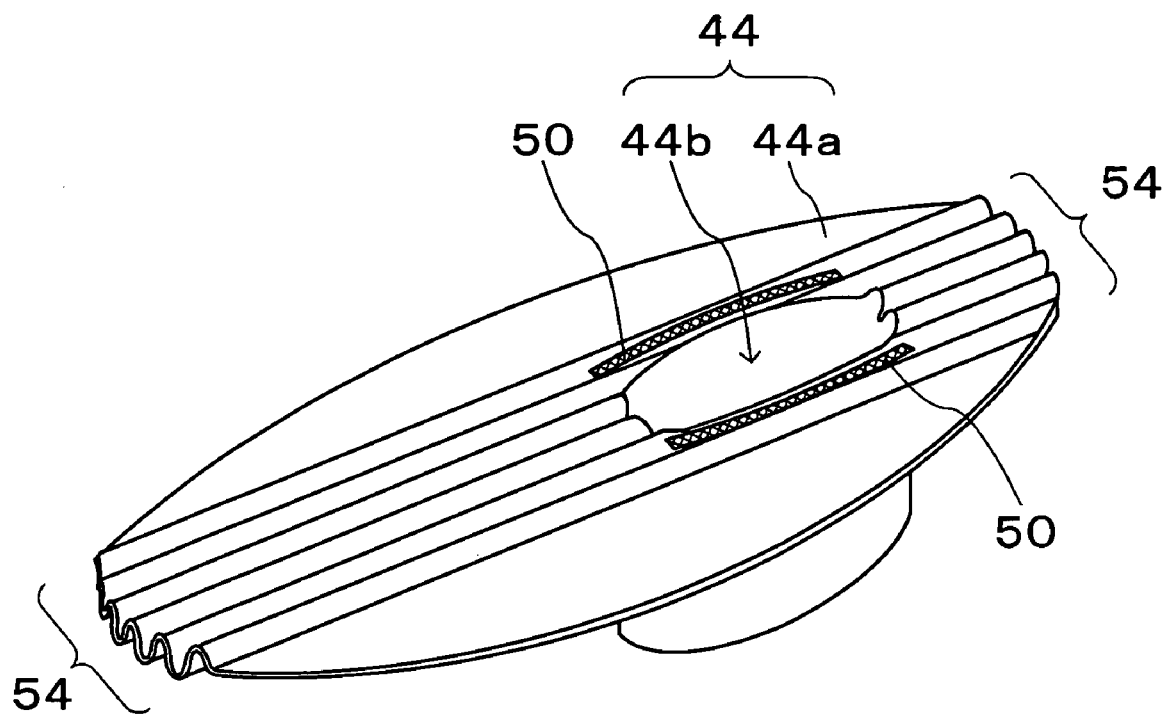
FIG. 8 is a perspective view showing the structure of the absorbent article according to the present invention.
Figure 9:
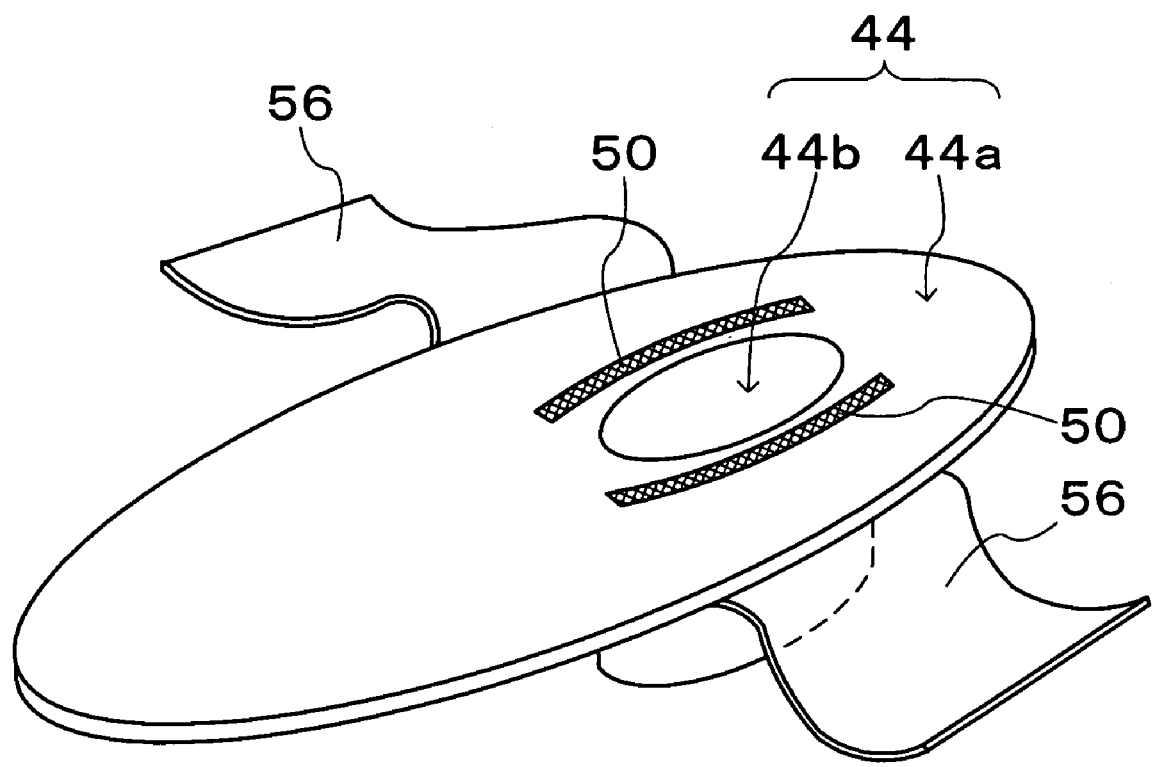
FIG. 9 is a perspective view showing the structure of the absorbent article according to the present invention.
Figure 10:
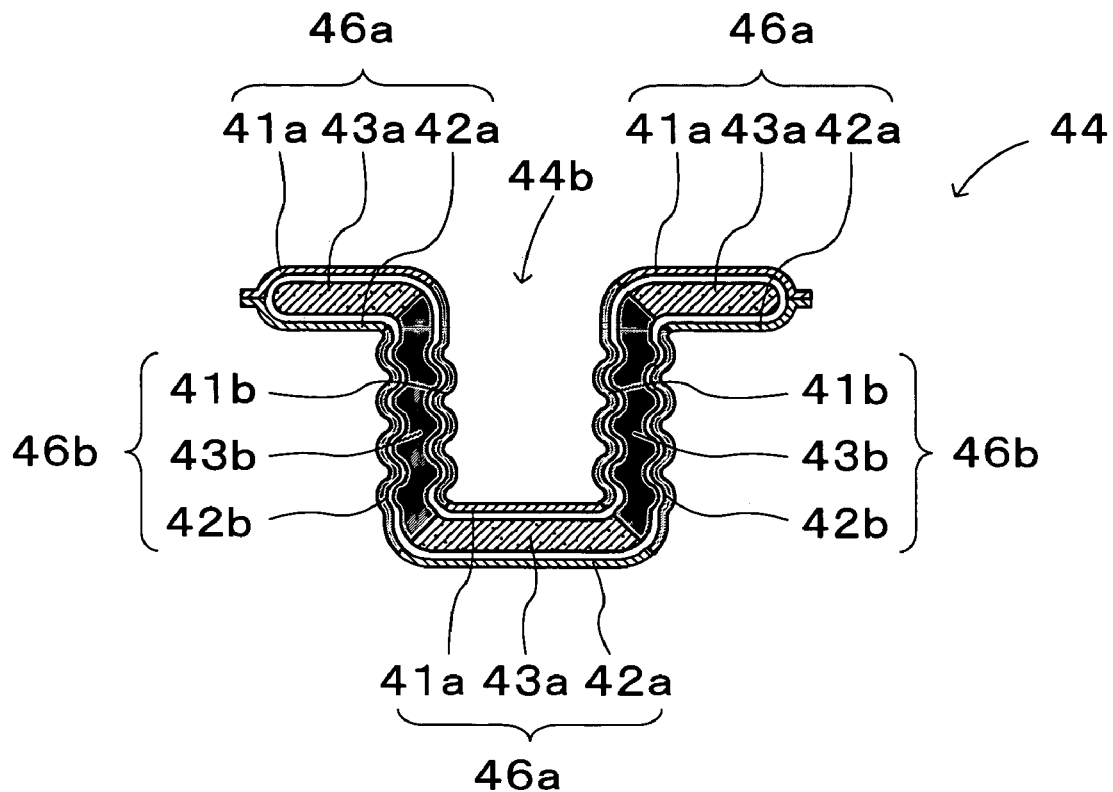
FIG. 10 is a cross sectional view showing the structure of the absorbent article according to the present invention.
Figure 11:
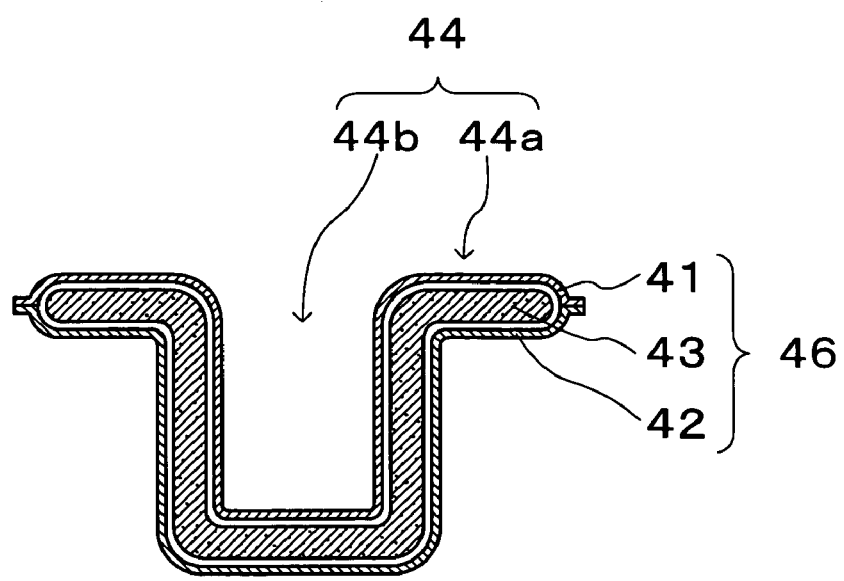
FIG. 11 is a cross sectional view showing the structure of the absorbent article according to the present invention.
Figure 12:
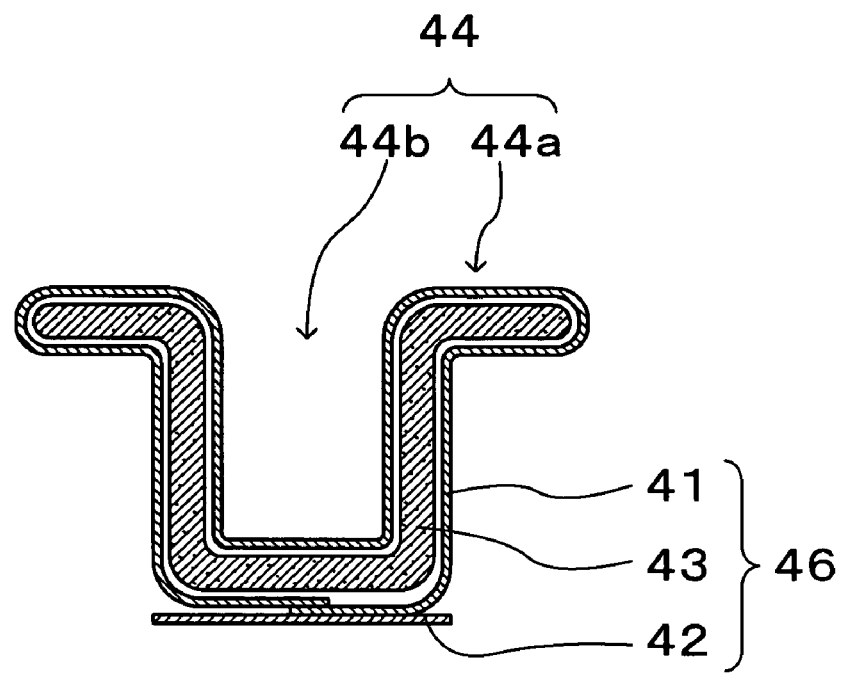
FIG. 12 is a cross sectional view showing the structure of the absorbent article according to the present invention.
Figure 13:
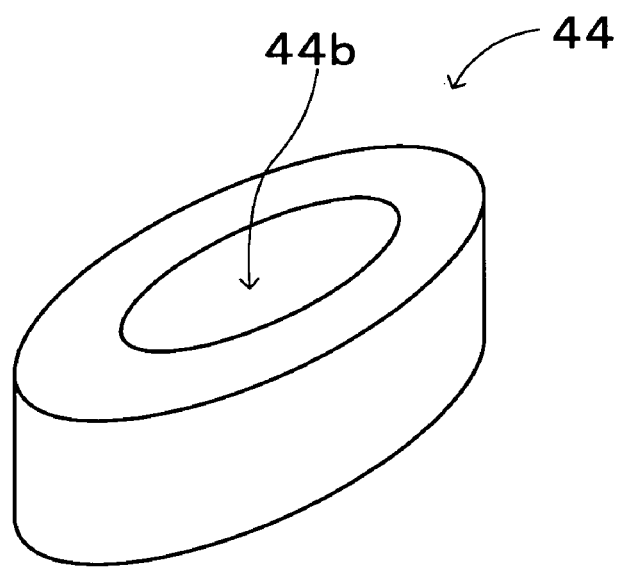
FIG. 13 is a perspective view showing the structure of the absorbent article according to the present invention.
Figure 14:
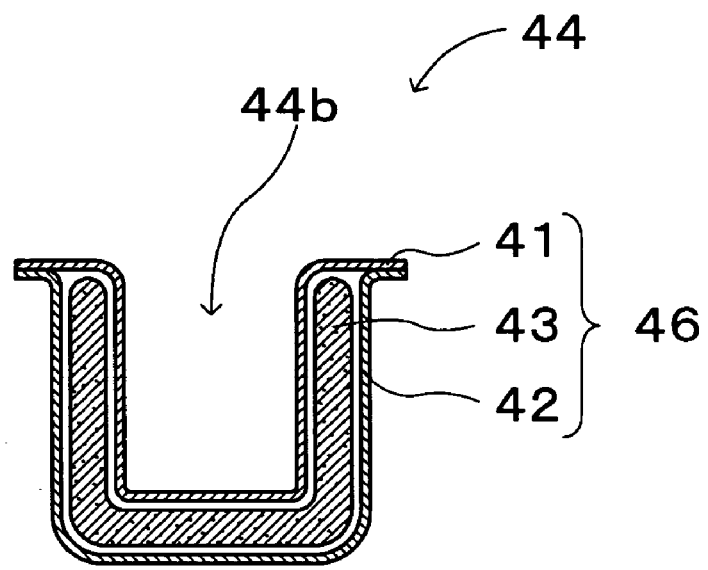
FIG. 14 is a cross sectional view showing the structure of the absorbent article according to the present invention.

FIG. 1(a) is a schematic top view showing an absorbent article 14 according to the present invention; FIG. 1(b) is a cross sectional view along A-A' of the absorbent article shown in FIG. 1(a).

[(A) Basic Structure of Absorbent Article]

The basic structure of an absorbent article 14 according to the present invention comprises, for example, as shown in FIG. 1(a) and FIG. 1(b), a body fluid inflow hole 14b for collecting the body fluid (especially the menstrual blood) provided in a part of a substantial by flat area 14a. The body fluid inflow hole 14b is a hole with a bottom on the garment side and the opening is formed to have the size sufficient to be fitted to cover a pair of labia majoras from the outside.

As for the overall shape of the absorbent article 14, it is preferable to be in a form with a substantially longer length in the longitudinal direction under consideration that the menstrual blood discharged from the ostium vaginae travels along the pudendal slit. Specifically, it may have an oval shape, an ovoid shape, a gourd shape, or a drop shape. Further, the so-called wing (for fixing the absorbent article by being adhered to underclothing) extended from the side edge direction of the absorbent article may also be formed.

It is necessary for the absorbent article 14 to have at least 150 mm or more in length (the size of the absorbent article in the longitudinal direction). However, it is preferable to be such a length so that the article does not interfere with the movement of thighs or haunches of the wearer when worn and, at the same time, no leak of the menstrual blood is generated. Specifically, it is preferable to be within the range of 200 to 400 mm and more preferable to be 210 to 300 mm. Also, it is preferable to have such width that the body fluid inflow hole can be formed and the wearing feeling is not affected. Specifically, it is preferable to be within the range of 50 to 120 mm and more preferable to be 60 to 100 mm.

The absorbent article comprises, for example, as shown in FIG. 1(b), a single or a plurality of absorbent sheet bodies 16 in which, a water permeable sheet 11 capable of permeating the menstrual blood, a water impermeable sheet 12 capable of preventing the leak of the menstrual blood, and an absorbent body 13 capable of absorbing the menstrual blood being included, the water permeable sheet 11 and/or the water impermeable sheet 12 are formed into one body. In general, an adhesive for fixing the absorbent article 14 to the underclothing is applied to the water impermeable sheet 12 which is positioned to face the garment side.

The water permeable sheet 11 and the water impermeable sheet 12 are bonded in a peripheral part 15 so as to include the absorbent body 13 by heat embossing and/or a hot melt adhesive.

When bonding the peripheral edges of the water permeable sheet 11 and the water impermeable sheet 12, it is preferable not to pinch the absorbent body 13 between the bonding parts. If the absorbent body 13 is pinched between the bonding parts, the peripheral edge 15 of the absorbent article 14 becomes stiff, so that the wearer may have the foreign feeling or uncomfortable feeling when wearing the article. In order for the absorbent body 13 not to be being pinched between the bonding parts, for example, the water permeable sheet 11 and the water impermeable sheet 12 may be bonded beforehand into a cell-like form with a part opened to be the opening and then put the absorbent body 13 into the cell-like form. The size of the absorbent body 13 may be the same as that of the absorbent article 14. However, it may be formed to be slightly smaller than the absorbent article 14 keeping the space of 2 to 10 mm from the outer frame of the absorbent article 14 so that the absorbent body 13 is not to be pinched between the bonding parts.

Further, the absorbent body 13 is adhered to the water permeable sheet 11 and the water impermeable sheet 12 so as to prevent the both sheets from being separated from each other. When using the absorbent article 14 (under wet environment due to the menstrual blood), above-described two members are easily separated. In order to avoid this, it is preferable to adhere the above-described members by heat embossing. By heat embossing, it is possible to achieve adhering in dots or screen pattern. By setting the rate of embossed area against the whole area to be in the range of 3 to 20%, it is possible to improve the strength when the article is used (under wet environment) without deteriorating the water permeability.

The shape of the opening of the body fluid inflow hole 14b may be selected from an oval shape, a rectangular shape, a gourd shape and the like whichever appropriate. However, under consideration of the shape fitness of the labia, it is preferable to be in the longitudinal oval shape or the shape as shown in FIG. 1(a). Also, inside the body fluid inflow hole 14b, it is preferable to form pores on the water permeable sheet 11 so that the menstrual blood is easily absorbed by the absorbent body 13. Thereby, the menstrual blood directly comes to be in contact with the absorbent body 13 to be absorbed through the pores (without traveling through the water permeable sheet 11).

[Water Permeable Sheet]

As for the water permeable sheet, the material which is soft, bulky and less stimulant to the sensitive labia may be selected from the group of sheet material with a structure that permeates liquid consisting of a fabric, a nonwoven fabric, a perforated plastic sheet and the like. Examples of such materials are a fiber sheet made of a nonwoven fabric such as spun bond, through-air, point bond, airlaid and the like, a film, a perforated plastic sheet in which a liquid-guiding duct is formed, and a foam sheet. The materials may be used alone or in combination.

Examples of the preferable materials of the water permeable sheet may be described in detail. For example, it is preferable to use a sheet obtained through bonding, by through-air, a fiber web (to be a first layer) made of a hydrophobic fiber (may be a filament or a bicomponent fiber with a sheath-core structure) with 1.1 to 3.3 dtex fineness and by a specific weight per unit of 10 to 25 g/m² and a fiber web (to be a second layer) made of a hydrophobic fiber to which a hydrophilic treatment is performed (may be a filament or a bicomponent fiber with a sheath -core structure) with 1.1 to 2.2 dtex and by a specific weight per unit of 15 to 35 g/m². More specifically, preferably used is a fiber sheet with bulkiness of 2.6 mm obtained through bonding, by through air, a bicomponent fiber with 2.2 dtex, which is made of PE (polyethylene) and PP (polypropylene) with 15 g/m² by a specific weight per unit and a fiber web made of the composite fiber 1.6 dtex and 25 g/m² to which hydrophilic treatment is performed.

Further, a foamed material may be preferably used as such material. This material may be obtained through a following procedure. First, a resin obtained by mixing PE and ethylene-vinyl acetate copolymer (EVA) by 80:20 mixing mass ratio is foamed by 15 expansion rate and then is formed into a sheet through crosslinking by electronic irradiation. Then, the sheet is cut in half so as to have the thickness of 1.5 mm. It is used in such a manner that the surface side is orientated to the body side of the absorbent article and the inner side to the absorbent body side (the center side of the absorbent article). It is preferable to apply a surface active agent to the inner side surface.

Furthermore, it is also preferable to use a composite material in which the body of the absorbent article is made of a melt blown nonwoven fabric and the center side of the absorbent article is made of a fiber sheet to which a hydrophilic fiber is mixed. This material can be obtained through the following procedure. First, a bicomponent fiber made of PE and PP with 2.2 dtex to which a hydrophilic treatment is performed, and a regenerated cellulose fiber with 1.5 dtex are mixed at 70:30 mass ratio. Then, a nonwoven sheet conditioned to be 20 to 40 g/m² by a specific weight per unit is prepared by applying a water-flow interlacing treatment. The composite material may be obtained by bonding, at 13% bonding area ratio, the nonwoven fabric sheet and the melt blown nonwoven fabric made of PP with 15 to 30 g/m² by a specific weight per unit. It is preferable that the specific weight per unit of the nonwoven fabric sheet be 25 g/m² and that of the melt blown nonwoven fabric be 25 g/m².

Furthermore, it is also preferable to use a composite material in which the body side of the absorbent article is made of a three-dimensional foam film and the center side of the absorbent article is made of a melt blown nonwoven fabric to which a hydrophilic treatment is performed. The three-dimensional foam film with 20 g/m² by a specific weight per unit contains an LDPE resin with the density of 0.915 g/cm³ as a main component and a 5 mass % of titanium oxide. The cross section of the liquid guiding duct forming the porous part has a tapered shape. The surface perforated ratio is 55% and the size of the pore is 0.28 mm². The above-described composite material is obtained by spraying the melt blown fiber made of PP as the main component in a melted state onto one of the face of the three-dimensional foam film and then conditioning it to be 25 g/m² by specific weight per unit, or by adhering the sheet of the melt blown fiber made of PP as the main component with 25 g/m² by a specific weight per unit by a heat embossing. It is preferable to perform a hydrophilic treatment on the part of the melt blown fiber by spraying or coating the surface active agent.

As for the inside of the body fluid inflow hole, the water permeable sheet as described can be preferably used. However, as has been described, it is preferable to use the following materials when intending to give elasticity to the side wall. An example of such material may be a composite melt blown nonwoven fabric in which a hydrophobic melt blown nonwoven fabric made of synthetic rubber type resin (for example, styrene ethylene•butadiene styrene block copolymer (SEBS), styrene isoprene styrene block copolymer (SIS), styrene butadiene styrene block copolymer (SBS), styrene ethylene•propylene styrene block copolymer (SEPS), polyurethane and the like) is provided on the body side of the absorbent article and a hydrophilic melt blown nonwoven fabric obtained by performing a hydrophilic treatment on the same synthetic rubber type resin is provided in the center side of the absorbent article.

As for the structure of the above-described composite melt blown nonwoven fabric, a specific example may be that the above-described hydrophobic melt blown nonwoven fabric conditioned to have 10 to 20 g/m² by a specific weight per unit and the above-described hydrophilic melt blown nonwoven fabric conditioned to have 10 to 30 g/m² by a specific weight per unit are bonded to each other at 8 to 20% bonding area ratio. The material is conditioned to have a contractive force of 600 to 1500 mN under 1.2 to 2.0 expansion rate so that the side wall portion of the body fluid inflow hole stands out.

In order to give an elasticity to the side wall, a band-form body or a string body made of the synthetic rubber type resin as described or the natural rubber as the main component may be adhered to the whole or a part of the side wall. This is adhered under the condition with a contractive force of 600 to 1500 mN under 1.2 to 2.0 expansion rate so that the side wall portion of the body fluid inflow hole stands out.

It is also preferable to adhere an elastic flexible material separately to the side wall of the menstrual blood inflow hole and the substantial flat area of the absorbent article. The opening can be well formed by conditioning b/a to be within the range of 0.8 to 0.9 provided that the expansion rate of the elastic flexible material to be adhered to the side wall of the menstrual blood inflow hole is (a) (where, (a) is selected from the range of 1.2 to 2.0 expansion rate) and the expansion rate of the elastic flexible material to be adhered to the substantial plane is (b).

[Absorbent Body]

It is preferable for the absorbent body, although any material can be used as long as it is hydrophilic, capable of absorbing and holding body fluid (menstrual blood), it is also preferable to be bulky, hard-to-be deformed, and less chemically stimulant. Moreover, considering that the absorbent article is fitted to the labia, it is preferable to highly flexible.

As for the fiber materials forming the absorbent body which is selected based on the above-described respects, a wood pulp, a natural cellulose fiber, a regenerated cellulose fiber and a fiber obtained by performing a hydrophilic treatment on a hydrophobic synthetic fiber are used. These fibers may be used alone or in combination where appropriate. Also, acrylic acid, graft copolymer of acrylic acid and starch, starch, carboxymethyl cellulose, particulate super absorbent polymer or super absorbent polymer fiber such as a foamed super absorbent polymer (foamed SAP) and the like, or a synthetic fiber (including a filament and a bicomponent fiber with a sheath -core structure) may be mixed.

In addition to the above-described materials, the material which can be preferably used as the absorbent body is a sheet material or a ground body of the following materials such as tissue, a foam sheet to which a hydrophilic treatment is performed, a melt blown nonwoven fabric to which a hydrophilic treatment is performed, a fiber web made of a hydrophilic fiber as the main component, a spun lace nonwoven fabric obtained by forming a fiber web into a sheet, a nonwoven fabric material such as a thermal bond nonwoven fabric, above-described "tow", an expanded foam made of a synthetic rubber to which a hydrophilic treatment is performed as the main component, and a cellulose sponge made of cellulose as the main component.

Also, under consideration of the fitness to the labia when the article is worn, for example, it is possible to use the laminated sheet of the perforated plastic sheet to which the liquid guiding duct is formed and a spun lace nonwoven fabric, or a material obtained by grinding the laminated sheet.

As for the more specific structure of the absorbent body, a sheet body may be used, which is obtained by the following procedure. First, a fiber web obtained by mixing 60 to 90 mass % of a regenerated cellulose fiber with 2.2 dtex and 10 to 40 mass % of a natural cellulose fiber is formed into a sheet body by a water-flow interlacing treatment thereby to obtain a spun lace nonwoven fabric. This sheet material alone, or a plurality of the sheets being laminated to have 50 to 500 g/m$^2$ (preferably, within the range of 150 to 400 g/m$^2$) by a specific weight per unit may be used.

Figure 15:
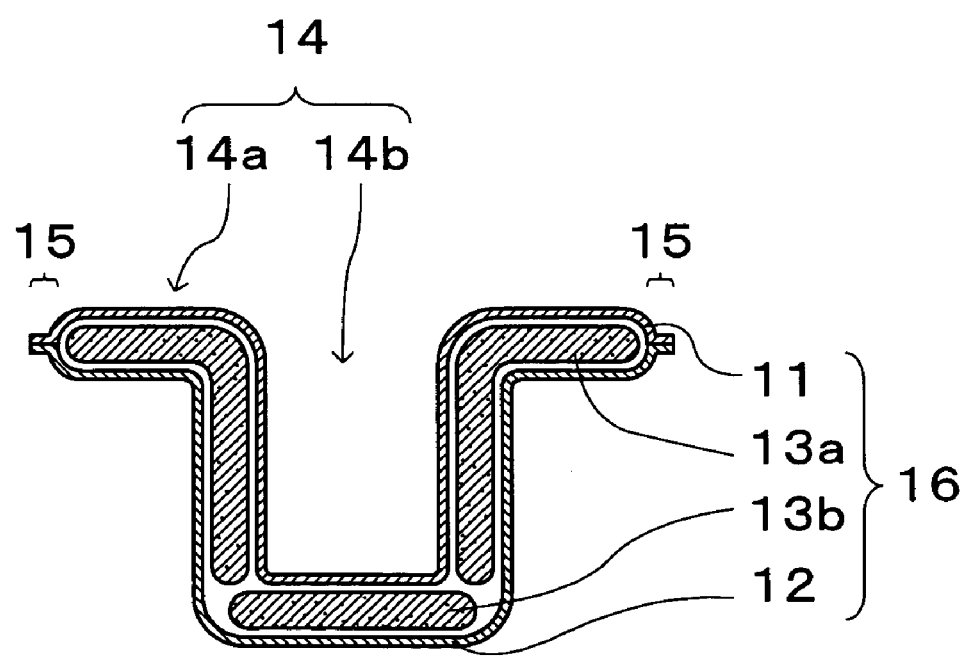
FIG. 15 is a cross sectional view showing the structure of the absorbent article according to the present invention.

As for the absorbent body, as shown in FIG. 1(b), the absorbent body 13 may be formed into one body or, as shown in FIG. 15, may be formed into a plurality of separate absorbent bodies 13a and 13b where appropriate.

[Water Impermeable Sheet]

As for the material used for the water impermeable sheet, it is necessary to be capable of preventing the leak of the menstrual blood held by the absorbent body to the outside of the absorbent article. It is preferable for the water impermeable material to be, in addition to being water impermeable, highly flexible. Specifically, examples of such material may be a film made of polyolefin resin (for example, low-density polyethylene (LDPE), linear low-density polyethylene (LLDPE), high-density polyethylene (HDPE) and the like) and a film made of a synthetic rubber (for example, SEBS, SIS, SBS polyurethane and the like).

It is preferable that the water impermeable material be the one with moisture permeability so that the stuffiness felt at the time of wearing the article can be decreased, thereby enabling to reduce the uncomfortable feeling. For example, preferably used are the so-called a moisture permeable film which forms minute cells through mixing inorganic filler and then performing a stretching treatment, a nonporous moisture permeable film made of polyester polyether block copolymer, a porous moisture permeable film which, while having a structure with pores, has air holes with the size through which the liquid hardly leaks out

[Adhesion Portion]

In general, the adhesion portion is positioned in the vicinity of the periphery of the body fluid inflow hole opening. Especially, when the elastic sheet body is interposed or a corrugation processing is performed, it is positioned not to be off the above-described part but within. Examples of the manner by which the adhesive is applied may be in; plame, dots, mesh, or lines. The positioning of the adhesive is not specifically limited as long as it is capable of fixing to the body. However, under consideration of the pubic hair present in front part of the labia, it is preferable to position the adhesive part in the vicinity of both side parts of the absorbent article in lines with a width of about 1 to 5 mm.

The "adhesion portion" can be formed through applying an adhesive to the water permeable sheet. Also, an adhesive tape may be cut into a desired shape to be adhered thereto. An example of the adhesive agent, which can be used in the present invention, may be a gel adhesive made of water soluble polymer, a crosslinking agent, a plasticizer and moisture. More specifically, examples of the water soluble polymer used herein are gelatin, sodium polyacrylate, polyvinyl alcohol, carboxymethyl cellulose and the like. Examples of the crosslinking agent are water soluble metallic salt such as calcium chloride and magnesium sulfate, and examples of the plasticizer are glycerol, wax, paraffin and the like.

In addition, the so-called pressure sensitive hot melt adhesive can be also used as an adhesive for forming the adhesion portion. The pressure sensitive hot melt adhesive is obtained by fusing and mixing the adhesion adder such as terpene resin or rosin resin and a plasticizer such as wax with a synthetic rubber resin as the main component, such as SIS, SBS, SEBS, and SEPS.

Further, a foamed melt, which is obtained by mixing air or nitrogen gas to a pressure sensitive hot melt adhesive by spraying when the adhesive is being melted, may also be an effective adhesive with high elasticity. In the foamed melt, a number of minute bubbles are formed inside by expansion of air or nitrogen gas and it can be applied as a foamed body with 3 to 20 expansion rate.

Further, a silicone resin adhesive can also be used. An example of the silicone resin adhesive is a mixture obtained by mixing a crosslinking agent such as metallic salt of platinum, molybdenum, or antimony and a plasticizer such as ester wax, glycerin, or machine oil and the like with a silicone resin and a fluorocarbon resin as the main component.

As described, there are many kinds of adhesives for forming the adhesion portion. However, if the application stability is taken into account, the pressure sensitive hot melt adhesive is preferable. The pressure sensitive hot melt adhesive with a high application stability can be prepared by fusing and mixing 15 to 25 mass % of SEBS, 15 to 35 mass % of plasticizer, and 40 to 70 mass % of adhesion adder. An antioxidant, antifluorescent or the like may be added to the pressure sensitive hot melt adhesive within the range of 0.1 to 1.0 mass %.

Further, it is preferable to use a composite adhesive layer in which two or more kinds of adhesives are laminated. For example, such a composite adhesive layer may be obtained by, on the top face of the foamed melt applied layer, applying another adhesive helically or spraying it. More specifically, an example of such a composite adhesive layer may be obtained by the following procedure. A nitrogen gas is mixed to a low-adhesion adhesive obtained by melt-mixing 25 to 50 mass % of SEBS, 25 to 40 mass % of a plasticizer and 10 to 50 mass % of an adhesion adder, and then another adhesive is applied onto the top face on which foamed melt is applied within the range of 20 to 100 g/m$^2$ at 5 to 15 expansion rate. This composite adhesive layer is preferable in respect that it has the texture with an excellent elasticity.

An example of valuation method of the adhesive strength will be described in detail. The valuation method is to measure the separation force (FIG. 16) and the shearing force of the adhesive (FIG. 17). It is carried out by using a constant speed expansion tensile tester and a stainless plate 71 of 80 mm in length×50 mm in width. As a preparation for the evaluation test, a test piece of a polyethylene film 72 having substantially the same size as the stainless plate 71, in which an adhesive 73 is applied within the range of 25 mm in width and 50 mm in length, is left for 30 minutes at room temperature (20° C.) beforehand. Subsequently, the polyethylene film 72 is put lightly over the stainless plate 71 so that the adhesive 73 comes to be in contact with the stainless plate 71, and a roller is applied once (one way only) by 30 g/cm² pressure force. Then, it is left for 30 minutes at a room temperature (20° C.) to fabricate a test piece.

Figure 16:
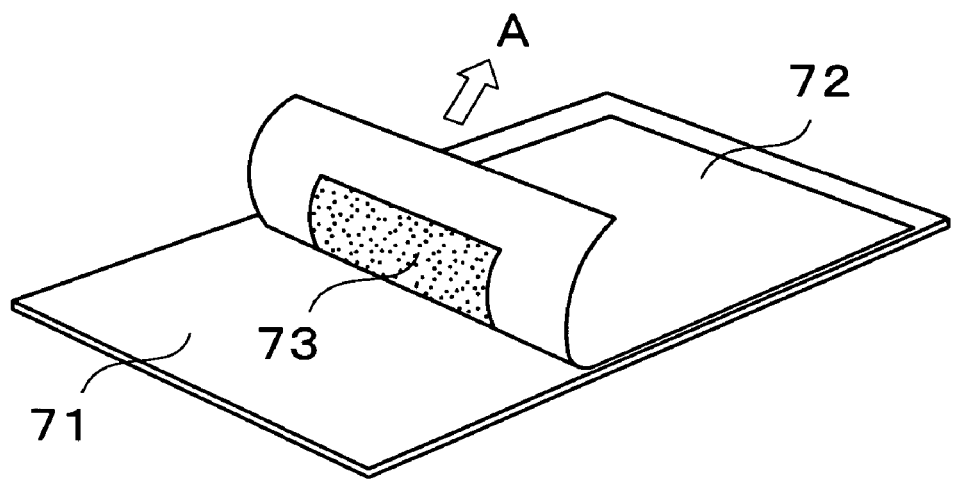
FIG. 16 is an illustration showing the experimental state for peeling strength measurement of an adhesive.
Figure 17:
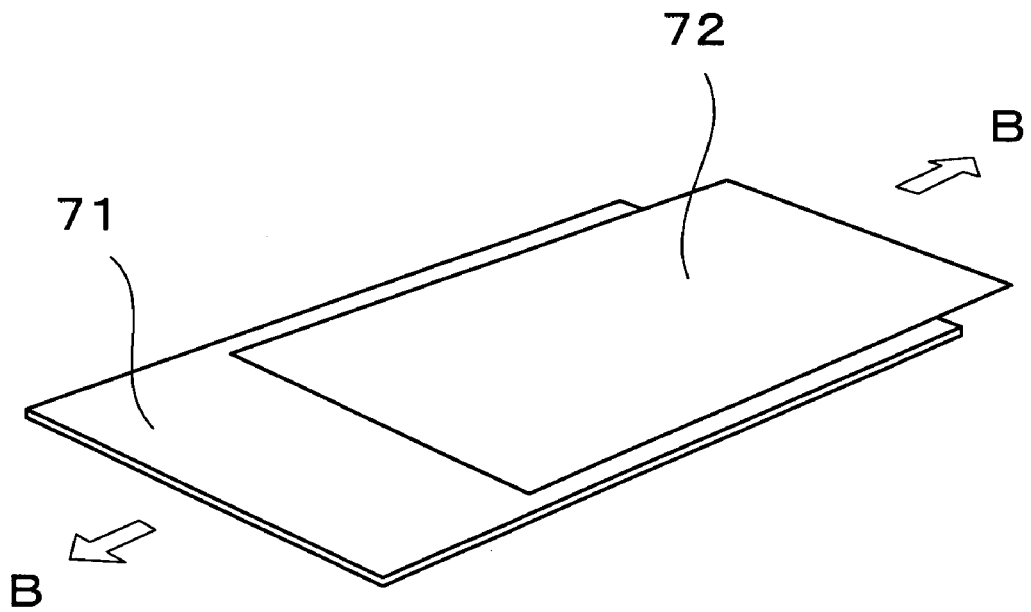
FIG. 17 is an illustration showing the experimental state for shear strength measurement of the adhesive.

The polyethylene film 72 part of the test piece obtained as described is, in the separation force test of the adhesive, separated in the pulling direction of an arrow A in FIG. 16 (180° separation). In the shearing force test of the adhesive, it is pulled in the pulling direction of an arrow B in FIG. 17. Where, the test condition is provided to be 100 mm/min testing speed.

In the case where the forces are measured by the method described above, it is preferable that the measurement value of the separation force be 100 to 2000 mN/25 mm and that of the shearing force be 3000 to 15000 mN/25 mm, under consideration of the burden imposed on the skin of the wearer.

As for the adhesion portion, it is preferable to cover the part to which the adhesive is applied with a sheet obtained by coating silicon resin on a thin paper, which is a generally obtainable separate paper, or a sheet obtained by coating silicon resin on a film. Thereby, damages or separation of the adhesive part can be prevented while being preserved before used.

[Elastic Sheet Body]

The elastic sheet body is positioned so as not to block the opening of the body fluid inflow hole. It uses the one with an opening being formed beforehand in the same size of the opening of the body fluid inflow hole or larger. The elastic sheet body is for preventing the adhesives for forming the adhesion portion from sticking to each other when fitting the opening of the body fluid inflow hole to the labia. Therefore, it is necessary to at least provide an area for forming the adhesion portion. Under consideration of keeping the comfortable state so as not to give an excessive wearing feeling to the wearer, it is preferable to use the one with the size of 10 to 20 mm longer in length and 10 to 20 mm wider in width compared to the size (60 to 180 mm in length and 20 to 60 mm in width) of the opening of the body fluid inflow hole.

It is necessary for the elastic sheet body not to deteriorate the adhesion force of the adhesion portion when the absorbent article is in wearing (under a wet environment due to the body fluid). Thus, it is preferable for the elastic sheet body to be repellent. Further, it is necessary that the elastic sheet body does not give a feeling of stiffness which affect the wearing feeling of the wearer. Therefore, it is preferable that the texture of the elastic sheet be 10 to 70 mm, which it is the values when measured by a cantilever in conformity with JIS and more preferable to be 15 to 40 mm.

Under consideration of the above-described conditions, it is preferable to use, as the material for the elastic sheet body, a fiber sheet, a film sheet, a foam sheet alone or a laminated material of the sheet materials which are formed into one body by a laminate processing. An example of the fiber sheet may be a nonwoven fabric sheet obtained by the following manner: a fiber with a PE/PP or PE/PET sheath-core structure and the fineness of 1 to 3.3 dtex is formed to a fiber web by carding and then it is formed into a sheet by heat embossing, through-air or water-flow interlacing treatment. It is preferable to apply a repellent processing on the surface of the nonwoven fabric sheet with a silicone resin, a fluorine compound and the like. Further, in order to reduce the stuffiness felt by the skin caused by the elastic sheet body, it is preferable to use, as the elastic sheet body, a nonwoven fabric sheet to which 5 to 30 mass % of a regenerated cellulose fabric is mixed.

Other examples of the fiber sheet may be a filament made of PP, PE or random copolymer of PP and PE, a spun bond nonwoven fabric (S) and a melt blown nonwoven fabric (M), which are made of a bicomponent fiber with PE/PP or PE/PET sheath-core structure, or a composite nonwoven fabric sheet obtained by composing S and M as in SMS and SSMMSS. Especially, an SMS composite nonwoven fabric sheet with 20 to 35 g/m² by a specific weight per unit obtained by bonding the sheet with the composing ratio of S:M:S=40:20:40 by the embossing area rate of 8 to 15% is preferable. This material has an advantage that the applied adhesive is hard to permeate and has an excellent stability of adhesive with time.

Examples of the film sheet and foam sheet may be a three-dimensional foam film, a laminated material of a film made of a synthetic rubber as the main component and a nonwoven fabric, and a foam sheet made of PE or a synthetic rubber as the main component. There are two types of foam sheet: one has a closed cell structure and the other has an open cell structure. The one with the closed cell structure is preferable since it is highly flexible. A foam sheet with a thickness of 0.5 to 2.0 mm and 5 to 20 expansion rate, which is obtained by foaming PE alone, or the mixture of PE and EVA, and then crosslinking it by irradiating electron beams, is one of the materials to be used preferably.

The elastic sheet body is bonded to the substantial flat area of the absorbent article by the bonding method such as a pressure sensitive hot melt adhesive, ultrasonic sealing, embossing sealing and the like so as not to be separated easily.

[(B) Structure of Absorbent Article to with Biodegradability, Water Dispersibility, and Water Solubility]

It is preferable that the absorbent article according to the present invention be formed of a biodegradable material and/or a water dispersible material and/or a water soluble material. Such absorbent article can be dropped off and flushed down to the toilet after use. Therefore, easy and clean disposal of the absorbent article can be achieved and trashes in the toilet can be further decreased at the same time.

In the present specification, "biodegradable" means that a substance is decomposed to carbon dioxide or a gas such as methane, water and biomass under anaerobic or aerobic condition according to the natural process under the existence of microbes including actinomycetes, and also means that the biodegradability of the synthetic material (biodegradable rate, biodegradable degree and the like) equals to a material naturally generated such as fallen leaves or a synthetic polymer which is generally recognized to have the same biodegradability under the same environment. "Water dispersibility" has the same meaning as being water degradability. It means a characteristic in which, while having no influence when used in a limited amount of moisture (menstrual blood), the fabric is easily dispersed into small pieces in a large amount of water or water current at least to a degree where an ordinal toilet plumbing is not clogged. "Water solubility" is a characteristic in which, while having no influence when used in a limited amount of moisture (menstrual blood), the fabric is soluble in a large amount of water or water current.

[Water Permeable Sheet]

As the material for the water permeable sheet with water permeability, both the natural fiber and the chemical fiber can be used. Examples of the natural fibers include cellulose such as pulverized pulp, cotton and the like, and airlaid pulp which is obtained by chemical-bonding these fibers with a water soluble resin. Examples of the chemical fibers are a regenerated cellulose such as rayon, feeble rayon and the like, a fiber obtained by performing a hydrophilic treatment on the chemical fibers such as PE, PP, PET, EVA and the like, the so-called biodegradable fibers such as poly lactic acid, polybutylene succinate and the like. Further, carboxymethyl cellulose, polyvinyl alcohol with water-solubility may be used. Among the materials described, it is preferable to use cellulose (pulp, cotton and the like), regenerated cellulose (rayon and the like), and the so-called biodegradable fibers such as polylactic acid.

The above-described materials may be used alone or in combination by being molded into a web or a nonwoven fabric. Web forming of the so-called biodegradable fibers such as polylactic acid, polybutylene succinate and the like may be performed by either a dry method through carding, spun bonding, melt-blown or airlaid, or a wet method, or a plurality of the methods in combination may be used. The methods of bonding may be thermal bonding, needle punching, chemical bonding and the like. However, it is not specifically limited to these. Further, a spun lace, which is formed in to a sheet by a water-flow interlacing treatment, may also be used.

Examples of the molding method for achieving water dispersibility may be a method in which hydrolysis paper is obtained by molding a fiber into a sheet through the hydrogen bonding of the fibers, a method in which hydrolysis paper is obtained by bonding the fibers through a water soluble binder and then molding it into a sheet, or a method in which hydrolysis paper is obtained by interlacing the fibers and then molding it into a sheet.

In order to keep an excellent water dispersibility, it is preferable to have the fabric length within the range of 2 to 51 mm, and more preferable to be within the range of 2 to 10 mm. Furthermore, in order to achieve both water dispersibility and a sufficient strength so as not to be damaged when it is used, it is desirable to select the fineness of the fiber (thickness) within the range of 1.1 to 4.4 dtex. Especially, when using rayon as the fiber, it is preferable to have the fineness within the range of 1.1 to 3.3 dtex. When it is less than the range, while an excellent water dispersibility can be achieved, raising and falling of the nap may be easily generated. On the other hand, when it exceeds the range, the water dispersibility is extremely deteriorated.

Also, it is preferable that the water permeable sheet has a specific weight per unit of 20 to 60 g/m$^2$. It is necessary that the breaking strength (the breaking strength when being stretched with specimen length of 100 mm and at a constant rate of extension of 100 mm/min) of the water permeable sheet in both longitudinal and lateral direction are at least 800 mN/25 mm, and preferable to be within the range of 1000 to 7000 mN/25 mm under consideration of the flexibility when worn.

A specific example of the water permeable sheet structure is a wet forming spun lace nonwoven fabric prepared by mixing 5 to 10 mm of rayon fiber with 1.1 to 4.4 dtex and wood pulp at 90:10 to 70:30 mass ratio conditioned to have 25 to 40 g/m$^2$ by a specific weight per unit and the thickness of 0.2 to 0.5 mm. In order to substantially improve the permeability for the menstrual blood (water permeability) or to give an image that it easily permeates the menstrual blood, a plurality of pores may be provided on the water permeable sheet. In this case, the pores may be formed to have a diameter within the range of 0.5 to 1.5 mm and the porous area ratio (rate of the porous area against the whole area) may be within the range of 3 to 20%.

[Absorbent Body]

As the material for the absorbent body, the same material as that of the water permeable sheet can be used. Further, it is also possible to use a material obtained by molding a single material or by mixing the materials selected from the group consisting of an absorbent material such as sodium alginate, starch, carboxymethyl cellulose, and a particulate super absorbent polymer or super absorbent polymer fiber.

A specific example of the absorbent body is a material prepared by enclosing wood pulp, after laminating it to have 150 to 500 g/m$^2$ by a specific weight per unit, to tissue and prepare it to the thickness of 2 to 10 mm by a pressing device. By mixing 5 to 30 g/m$^2$ of an absorbent material such as starch with the above mentioned absorbent body, it is possible to also improve the absorption and holding capacity of menstrual blood.

[Water Impermeable Sheet]

Specific examples of the water impermeable material may be cellulose derivative such as methyl cellulose, hydroxyethyl cellulose, and carboxymethyl cellulose, water soluble polymer such as polyvinyl alcohol, sodium alginate, sodium poly acrylate, polyacrylic ether, polyvinyl pyrrolidone, and a copolymer of isobutylene and maleic anhydride, or biodegradable polymer such as poly lactic acid, polybutylene succinate, starch, and dextrin.

These materials may be molded into a melt blown nonwoven fabric or a film sheet by using alone or combination with these materials. Furthermore, a repellent material such as silicone resin may be applied or mixed in thereto or a laminate processing may be performed on a nonwoven fabric.

A specific example of the water impermeable sheet structure is a film obtained by preparing polyvinyl alcohol with 20 to 50 g/m$^2$ by a specific weight per unit to which 0.5 to 5 μm silicone resin or fluorocarbon resin is applied at least on either side and, more preferably, on both sides.

[Bonding Method]

As the bonding method applicable in the present invention, boding by polyvinyl alcohol and the like, with water solubility or water dilatation characteristic, heat sealing, hydrogen bonding may be used alone or in combination where appropriate.

INDUSTRIAL APPLICABILITY

As described, the absorbent article according to the present invention is provided with a body fluid inflow hole. Therefore, it can prevent the side leak of the body fluid such as the menstrual blood, so that the garment can be prevented from being stained. Further, the contact between the discharged body fluid and the skin can be prevented, thereby achieving a comfortable wearing feeling.

What is claimed is:

1. An absorbent article comprising:
    an absorbent sheet body, the sheet body integrally including a water permeable sheet facing a body side of a wearer and either a water permeable or water impermeable sheet facing a garment side such that an absorbent body that absorbs body fluid body fluid is contained between the sheets, wherein the article is applied to a pubic region; and
    a body fluid inflow hole formed on the absorbent sheet body being depressed into a cylindrical shape with a bottom at the garment side and an opening at the body side with a size capable of fitting a pair of labia majoras from outside such that the pair of labia majoras pass through the opening, wherein the cylindrical shape of the body fluid inflow hole has a hollow part, a side wall portion of the body fluid inflow hole protrudes downward toward the garment side to form a flange, and the side wall of the body fluid inflow hole includes an elastically restoring material, and further comprising an adhesion portion surrounding a periphery of the opening of the body fluid inflow hole on a body side face, and wherein folded pleats are formed that are located around said adhesion portion and that extend along an entire longitudinal length of the article.

2. The absorbent article according to claim 1, wherein the adhesion portion is divided into left and right parts with respect to a substantial center line of the absorbent article along a longitudinal direction.

3. The absorbent article according to claim 1, further comprising an elastic sheet body made of an elastically restoring material being interposed between the body side face of the absorbent article and the adhesion portion.

4. The absorbent article according to claim 1, further comprising an attachment tab of a band shape extending out from a side edge of the adhesion portion.

5. The absorbent article according to claim 1, wherein:

the absorbent body is contained in the water permeable sheet; and the garment side face on the bottom of the body fluid inflow hole is lined with the water impermeable sheet.

6. The absorbent article according to claim 1, wherein the absorbent article is for incontinence.

7. The absorbent article according to claim 1, wherein the absorbent article is for absorbing vaginal discharge.

* * * * *